US008859743B2

(12) United States Patent
Franzin et al.

(10) Patent No.: US 8,859,743 B2
(45) Date of Patent: Oct. 14, 2014

(54) CONTROLLING MICROBIAL CONTAMINATION IN ALCOHOLIC FERMENTATION PROCESS

(75) Inventors: Mauricio da Silva Franzin, Paulo (BR); Maria Regina Prioli, Alpharetta, GA (US)

(73) Assignee: Arch Chemicals, Inc., Norwalk, CT (US)

( * ) Notice: Subject to any disclaimer, the term of this patent is extended or adjusted under 35 U.S.C. 154(b) by 214 days.

(21) Appl. No.: 13/138,323

(22) PCT Filed: Feb. 11, 2010

(86) PCT No.: PCT/US2010/023853
§ 371 (c)(1), (2), (4) Date: Sep. 19, 2011

(87) PCT Pub. No.: WO2010/093765
PCT Pub. Date: Aug. 19, 2010

(65) Prior Publication Data

US 2012/0009639 A1 Jan. 12, 2012

(30) Foreign Application Priority Data

Feb. 12, 2009 (BR) ..................................... 0900238

(51) Int. Cl.
*C07G 11/00* (2006.01)
*C12P 7/02* (2006.01)
*C12N 1/18* (2006.01)

(52) U.S. Cl.
CPC .. *C12N 1/18* (2013.01); *Y02E 50/17* (2013.01)
USPC .......................................... 536/16.8; 435/155

(58) Field of Classification Search
None
See application file for complete search history.

(56) References Cited

U.S. PATENT DOCUMENTS

| | | | | |
|---|---|---|---|---|
| 2007/0048344 | A1* | 3/2007 | Yahiaoui et al. | 424/405 |
| 2007/0082041 | A1 | 4/2007 | Walters et al. | |
| 2007/0225189 | A1 | 9/2007 | Dailey et al. | |
| 2008/0003660 | A1 | 1/2008 | Bayrock et al. | |
| 2008/0142453 | A1* | 6/2008 | Unhoch et al. | 210/755 |

FOREIGN PATENT DOCUMENTS

| | | | |
|---|---|---|---|
| WO | 2009001205 | A2 | 12/2008 |
| WO | 2010093765 | A1 | 8/2010 |

OTHER PUBLICATIONS

Glucopon 220UP Product data sheet (last viewed on Sep. 26, 2013).*
Bailey et al., Improved Homogenization of Recombinant *Escherichia coli* following Pretreatment with Guanidine Hydrochloride., Biotechnology Progress (1995), vol. 11, Issue 5, pp. 533-539.*
CaltechThesis, last viewed on Sep. 26, 2013.*
What is the chemical composition of Dog Urine? (last viewed on Sep. 26, 2013).*
Structure of genapol (last viewed on Feb. 19, 2014).*
Buxbaum et al., Antimicrobial and teoxicological profile of thenew biocide Akacid plus®., Journal of Antimicrobial Chemotherapy (2006), vol. 58, pp. 193-197.*
Elsztein, Carolina et al., "*Polyhexamethyl biguanide can eliminate contaminant yeasts from fuel-ethanol fermentation process*," J. Ind Microbiol Biotechnol, vol. 35, pp. 967-973 (2008).
Bello, Fabio Dal et al, "*Inducible Gene Expression in Lactobacillus reuteri LTH5531 during Type II Sourdough Fermentation*, "Applied and Environmental Microbiology, vol. 71, No. 10, pp. 5873-5878 (2005).
Elsztein et al., "Polyhexamethyl biguanide can eliminate contaminant yeasts from fuel-ethanol fermentation process", J. Ind. Microbiol. Biotechnol., vol. 35, No. 9, 2008, pp. 967-973, XP019596371.
Bello et al., "Inducible Gene Expression in *Lactobacillus reuteri* LTH5531 during Type II Sourdough Fermentation", Appl. Environ. Microbiol., vol. 71, No. 10, 2005, pp. 5873-5878, XP008150974.
Written Opinion of PCT/US1023853 dated Mar. 22, 2010.

* cited by examiner

*Primary Examiner* — Alexander Kim
(74) *Attorney, Agent, or Firm* — Miles & Stockbridge, P.C.

(57) ABSTRACT

The control of the microbial contamination during the sugar fermentation in the processes for obtaining alcohol is a very important action to increase the productivity of the alcoholic fermentation processes. The *Saccharomyces cerevisiae* yeast cells engage a very tough nutritional competition for the sugarcane juice with the bacteria (*Lactobacillus* sp and *Acetobacter*) and the wild yeasts. The proposed composition uses an antimicrobial agent of the guanidine family, such as for example, poly(hexamethyl biguanide), an antibiotic agent, and also a surfactant agent, to prevent the undesired microbial growth. The present invention further refers to the process for controlling the microbial contamination through the use of said agents.

9 Claims, No Drawings

CONTROLLING MICROBIAL CONTAMINATION IN ALCOHOLIC FERMENTATION PROCESS

CROSS-REFERENCE TO RELATED APPLICATIONS

This application is a U.S. National Stage application of International Application PCT/US2010/023853 filed 11 Feb. 2010.

FIELD OF THE INVENTION

The present invention relates to an antimicrobial composition and to a process for controlling the microbial contamination in alcoholic fermentation processes, particularly in the ethanol production from sugarcane.

BACKGROUND OF THE INVENTION

Despite the improvements introduced in the fermentation processes in the last years, they still do not present satisfactory performance with reference to the contamination control, due to the difficulty and the high costs regarding the control of the contamination levels of the raw material which is brought to the mill and processed to form the must to be fermented.

Nowadays, the characteristics of the sugarcane processing in the alcohol production mills typically lead to the occurrence of a bacterial microbiota which usually surpasses $10^4$ cells/ml in the fermentation must. Also, the same must, being a medium favorable to the bacterial growth, carries a varieties of contaminant bacteria such as *Lactobacilli* and wild yeasts besides the fermentative yeasts *Saccharomyces cerevisiae*.

The presence of contaminants may causes a decrease in fermentation productivity and other operational problems. For example, wild yeasts, can compete with the fermentative yeasts, absorbing the sugar in the must to be fermentated without converting it to alcohol.

Additionally, the presence of bacteria, *Lactobacilli* and wild yeasts in the fermentative must tends to provoke agglomeration of these organisms around the fermentative yeasts, thus producing flocculation and impairing the productive activity of the fermentative yeasts.

It should be further observed that, with the increase of the bacterial and *Lactobacilli* density in the fermentation must, the organic acid concentrations tend to become excessively high. The high organic acid concentration inhibits the multiplication of the fermentative yeasts, which can reduce the productivity of the industrial plants for about 10-20%. In cases of more severe contaminations, higher decreases of ethanol productivity can be observed.

Heretofore, antibiotics have been widely used to control the fermentation must contamination. However, the efficiency of the antibiotics is normally limited to a certain group of bacteria. For example, although the currently available antibiotics have specific action which is desirable against the Gram-positive bacteria and *Lactobacilli*, they have the reduced action against the wild yeasts. Thus, the use of the antibiotics does not eliminate the productivity losses resulting from the presence of wild yeasts in the fermentative must because the wild yeasts compete with the fermentative yeasts for the sugar contained in the must to be fermented.

In addition, the antibiotics are of slow action in the fermentative must. This characteristic of antibiotics allows the growth of the wild yeasts, bacteria and *Lactobacilli* sp during an initial phase of antibiotic action. Accordingly, a high antibiotic load is normally required to control the increasing degree of bacteria and *Lactobacilli* contamination of the fermentative must. Besides, over time, more and more bacteria develops antibiotic resistance, which may also require high loads of antibiotics to obtain acceptable productivity levels.

Antibiotics are normally expensive, increased antibiotic loads may bring the fermentation cost to an unacceptable level. Moreover, higher loads of antibiotics can also cause allergies and other diseases affecting the operators involved with this phase of the process. Further, there is an increasing demand from the consumers in sub-products resulted from the fermentation process for these products to be ecologically friendly and cause no harm to the human being and the environment. This translates to a demand for increasingly smaller residual amounts of antibiotics in the product.

As a consequence of the limitations and inconveniences related to the use of the antibiotics for controlling contaminants, attempts have been made to develop an agent capable of minimizing the deficiencies commented above, some of which are inherent to the use of high loads of antibiotics, while at the same time being effective in reducing the negative effects of the bacteria, *Lactobacilli* and wild yeasts presented in the fermentative process.

The use of biguanide compounds as antimicrobial agents for inhibiting the growth of contaminant microorganism canker microbe on plants is known. Brazilian patent application PI 0505795-7 (corresponding to the North-American patent application U.S. 60/640,595), to Ecolab, Inc. disclosed a composition for reducing the population of canker microbe (for example, citrus canker microbes), on a series of objects, such as, citrus plants, fruits, seeds, cut flowers, etc. According to the specification, the antimicrobial composition may include a metal antimicrobial agent, for example, silver ion, and a polymer, for example, a poly(hexamethyl biguanide) (PHMB). This composition has bacteriostatic and/or biocidal action and helps in controlling canker growth by applying the antimicrobial composition in an amount and for a time sufficient to reduce the microbial population.

However, the action of the biguanide compound or poly (hexamethyl biguanide)(PHMB) in the Ecolab composition is obligatorily associated with another inorganic antimicrobial agent, so that it can effectively have the antimicrobial function in the "object", in certain amounts of said agent in the mixture of the components which form the composition, for reducing the population of plant pathogens. Although the silver-based inorganic compounds are known in the prior art, their use in the formation of compositions for controlling the microbial contamination in alcoholic fermentation processes is economically unfeasible, making the prior art proposal inadequate to be used in alcoholic fermentation media for obtaining ethanol.

Another application of the polyhexamethylene biguanide (PHMB) is described by Elszetin, C. and Morais, M. A., in an article entitled "Polyhexamethyl biguanide can eliminate contaminant yeasts from fuel-ethanol fermentation process" published at J. Ind. Microbiol. Biotechnol., (2008), 35:967-973. In the article, the authors examined the fungicidal activity of the poly(hexamethyl biguanide) (PHMB). Based on the effects of PHMB upon growth inhibition and microorganism kill, evaluated in laboratory cultures and industrial samples, the authors proposed the use of PHMB at 200 mg/l to control the main fuel-ethanol contaminants on an industrial scale.

According to the article, the fungicidal effect of PHMB was tested in cells of *Saccharomyces cerevisiae* strains (JP1 and P2) and wild yeasts of *Dekkera bruxellensis*, collected directly from the industrial processes. Although these results demonstrate that the presence of PHMB reduces *D. bruxel-*

*lensis* below 1 log (44%) at table 2, page 971, the results also show that fermentative yeast *S. cerevisiae* PE2 is very sensitive to PHMB at concentrations above 20 ppm. Accordingly, the authors recommend using PHMB in combination with a high-fermentating PHMB-resistant strain. Also the authors recommend using PHMB biocide alone in the pre-fermentation vessels, where yeast biomass is aerated and fed with diluted cane juice, to prevent or reduce any negative effects of PHMB on the *S. cerevisiae* cells when they are exposed to sucrose and to low amount of ethanol.

While demonstrating the PHMB activity as a biocidal agent in distinct applications, the solutions met so far did not take into account the lethal effect of the proportions/concentrations suggested therein, for both the widely used antibiotics and the poly(hexamethyl biguanide) compound, on the fermentative yeasts *S. cerevisiae* themselves.

Recently, international patent application WO 2009/001205 A2 disclosed a method of producing fermentation-based products, particularly ethanol, comprising fermenting a sugar-containing medium with yeasts in the presence of an additive, for example, guanidine-based compounds, such as PHMB, alone or in combination with other organic biocides such as aliphatic and aromatic monoaldehydes and dialdehydes etc. to reduce or control a bacterial population in the sugar-containing medium.

Although the available prior art can lead to good results in the microbial control in the fermentation medium and also to a reduction in the residual amounts of antibiotics in the sub-products (dry yeasts), none of the prior compositions or methods lead to an increased preservation rate of *S. cerevisiae* yeast together with an increased elimination rate of the wild yeast, *Lactobacilli* and other bacteria in the fermentation medium, in order to allow unexpected productivity rates in fermentation processes.

Another drawback of the known processes results from the use of acid for treating the mixed juice received in the mill and for treating the yeast remaining from the fermentation of a load of must to eliminate the bacteria that remained alive after the fermentative process, thus allowing the yeast to be used in the fermentation of a new load of must. The use of acids has a series of drawbacks, such as the need to provide equipment resistant to the acid attack, increased cost associated with greater amounts of acid needed to treat high loads of bacteria remaining in the yeast being reused, the toxicity of this acid input, and the need to eliminate the acid from the sub-product (dry yeasts) of the fermentative process, particularly when used in the animal ration production.

None of the known alcoholic fermentation industrial processes succeeds in satisfying, in an economically feasible manner, all the new current demands that are related to the efficiency of the fermentative process, to the reduction of the loads of antibiotics to be employed in the process, to the level of residual bacteria and antibiotics in the subproduct (dry yeasts), and also to the reduction of the amount of acid, generally sulphuric acid, used for treatment of the yeast, due to the residual bacteria which can be found therein.

SUMMARY OF THE INVENTION

In view of the prior art limitations, the invention aims to provide an antimicrobial composition which can be applied to the must contained in the fermenting vats for alcohol production, for controlling the contamination by wild yeasts, *Lactobacilli* and bacteria present in the material under fermentation, preserving the fermentative yeasts from competing, with said contaminant microorganisms, for the nutrient available on the substrate, and allowing an increased productivity in fermentation processes and the use of reduced loads of antibiotics in the fermentation medium.

The antimicrobial composition object of the invention comprises an antimicrobial agent of the guanidine family, as for example, poly(hexamethyl biguanide) (PHMB); an antibiotic agent, and a surfactant agent, in adequate amounts sufficient to control the wild yeast, *Lactobacilli* and bacteria microbiota contained in the must to be fermented; to produce a defloculation effect in said must; and to preserve the fermentative yeasts from the competition, with the microbiota of contaminants, for the sugar contained in the must to be fermented.

The invention further refers to the method for controlling the microbial contamination in the alcoholic fermentation media, in order to obtain ethanol and/or other products derived from fermentation, by adding, to a load of must to be fermented, the biocidal, antibiotic and surfactant agents mentioned above in amounts adequate and sufficient to control the wild yeast, *Lactobacilli* and bacteria microbiota contained in the must to be fermented; to produce a defloculation effect in said must; and to preserve the fermentative yeasts from the competition, with the above contaminants, for the sugar contained in the must to be fermented.

Another aspect regarding the currently known treatments results from the fact that the load of dry yeast, which is withdrawn at the end of the fermentative process and processed to be returned to a new fermentation, presents a bacteria load that has resisted to the antibiotic action and which needs to be neutralized in order not to be re-introduced in a new fermentation batch.

With the combined action of the agents described above the performance of the fermentative yeast in use and free from the microbiota of contaminants is improved, and concerning the contamination, this yeast will have a reduced number or no bacteria, thereby reducing the necessary amounts of acid, generally sulphuric acid, for treating residual bacteria in dry yeast, and which is highly problematic in the mills.

DETAILED DESCRIPTION OF THE INVENTION

One of the generic objects mentioned above is achieved by the provision of an antimicrobial composition comprising: from about 1% to about 5% by weight of an antimicrobial agent of the guanidine family, as for example, poly(hexamethyl biguanide) (PHMB); from about 0.05% to about 0.5% by weight of an antibiotic agent; and from about 98.95% to about 94.5% by weight of a surfactant agent.

The antibiotic agent is generally selected as a function of the characteristics of the must under fermentation and of the contaminant microorganisms (microbiota of contaminants) found in said must, and also the conditions to which the raw material is submitted until reaching the fermentation vats.

Considering the fermentation of a sugarcane juice must ("garapa"), the antibiotic used to form the present antimicrobial composition can be an ionophor selected from virginiamycin, penicillin, penicillin V, clindamycin, lactamic acid, beta-lactamics, tetracycline, and particularly monensin, such as that one known by the commercial name Kamoran, from Elanco, in the percentages by weight of the composition, as mentioned above.

The biocide used in the present composition, in the percentages defined above, is an antimicrobial agent of the guanidine family, poly(hexamethyl biguanide) (PHMB), whose biocidal/bactericidal function is known from the prior art. The PHMB used in the present invention is commercially known as "Vantocil IB", manufactured by the present applicant.

Aiming to increase even more the efficiency of the fermentative process, the antimicrobial composition comprises an appropriate non-ionic surfactant agent, including alkoxylated alcohols, preferably ethoxylated alcohols.

Particularly, the active compounds of the appropriate non-ionic surfactant agents can be broadly described as compounds produced by the condensation of the alkylene oxide groups, which are hydrophilics in natura (as found in nature), with an organic hydrophobic compound, which may be aliphatic or alkyl aromatic in natura (as found in nature). The length of the hydrophilic or polyoxyalkylene radical which is condensed with any particular hydrophobic group can be easily adjusted to yield a water-soluble compound, having the desired balance degree between the hydrophilic and hydrophobic elements. The preferred alkoxylated alcohols are selected from the group comprising ethoxylated alcohols of the general formula: $R—(OCH_2CH_2)—N—OH$, wherein R is linear or branched, $C_8$-$C_{18}$ is alkyl or hydroxyalkyl and N is, on average, 1-14. The appropriate alcohols for use in the present invention include, for example, a coconut fatty alcohol and/or a polyglycol ether, preferably that known by the commercial designation "Genapol", produced by Clariant, there being also used cationic surfactants, amphoteric surfactants and other non-ionic types of surfactant agents.

It should be understood that different types of surfactants can be used to increase the dispersion degree of the active biocides and the degree of the deflocculation of the fermentative yeasts in the must and, thereby, the contact surface area of said yeasts with the sugar.

The use of antibiotics and PHMB in the concentrations defined above allows the PHMB to act innocuously on the fermentative yeasts, but effectively on the wild yeasts and contaminant bacteria (*Lactobacilli* sp and *Acrobacter* sp) contained in the fermentative must, immediately after applying the composition to control the contaminants.

The presence of the PHMB on the antimicrobial composition as a control means, in duly limited concentrations, to avoid its deleterious action on the fermentative yeasts, allows this biocide to act rapidly on the wild yeasts and even on a great number of contaminant bacteria susceptible to its bactericidal action, preventing said contaminants from competing for the fermentative must nutrients (sugar) with the productive yeasts.

An important aspect of this PHMB action on the wild yeasts and on the contaminant bacteria results from the fact that this action is immediate after application of the composition, i.e., the PHMB starts its biocidal/bactericidal action in less than five minutes, provoking the reduction of the wild yeasts and the control of the bacteria susceptible to its action, and preventing the proliferation of said contaminants and reducing their agglomeration action on the fermentative yeasts.

With the immediate action of PHMB on the contaminant microorganism, the action and proliferation of the wild yeasts and contaminant bacteria are interrupted, reducing the volume of bacteria to be specifically attacked by the antibiotic which presents an action considerably slower than that of the PHMB, and which is from about 3 to 5 hours. Thus, the load of antibiotics to be taken to the fermentative process can be substantially reduced to values compatible with the bacterial microbiota remaining in the fermentative must.

Further from the action of the antimicrobial and antibiotic agents on the microbiota of contaminants contained in the must to be fermented, it should be noticed that the presence of the surfactant agent in the composition allows to obtain a defloculation action in the must to be fermented, providing a separation not only of the particles of the fermentative yeast but also of the particles of the contaminant microbiota. This defloculation increases the contact superficial area of the fermentative yeast with the must (sugar) and also the contact superficial area between the contaminants and the antimicrobial and antibiotic agents, allowing an increase in the action of the agents on the contaminant microbiota and also a better fermentative efficiency of the yeast increasing the productivity of the fermentative process.

A possible formulation of the present antimicrobial composition comprises from about 1% to about 5% by weight of an antimicrobial agent of the guanidine family, poly(hexamethyl biguanide) (PHMB); from about 0.05% to about 0.5% by weight of an antibiotic agent; and from about 98.95% to about 94.5% by weight of a surfactant agent, considering that the recommended dose of said composition is situated about 0.052% by weight or 520 ppm, of the load of must in fermentation.

The present invention has also as object to provide a process for controlling the microbial contamination in alcoholic fermentation processes, particularly in the production of ethanol and/or other products derived from the fermentation of sugarcane. The process comprises the step of adding to the fermentation must, the following amounts by weight of the load of must in fermentation: about 5 ppm to about 26 ppm of an antimicrobial agent of the guanidine family, as for example, poly(hexamethyl biguanide) (PHMB); about 0.26 ppm to about 2.6 ppm of an antibiotic agent, as previously defined for the formulation of the antimicrobial composition, and further, about 491 ppm to about 514 ppm of the surfactant agent selected from the groups previously defined in relation to the antimicrobial composition.

Besides the great economic and environmental benefits resulting from the substantial reduction of the load of antibiotics, the provision of PHMB in the present control composition reduces, since the beginning of the fermentative process, wild yeasts and bacteria microbiota from agglomerating in the fermentative yeast, impairing the contact of the yeast with the nutrients (sugar) of the must and the productivity of the fermentative process.

Further, with the combined action of the surfactant agent of the present composition, together with the action of the PHMB and antibiotic, the flocculation in the fermentative must is avoided, allowing a very high degree of contact of the fermentative yeast with the nutrients (sugar) contained in the must increasing the efficiency of the fermentative process.

With the composition of the invention described above, the performance of the fermentative yeast is improved. In addition, the dry yeast will have a reduced number or no bacteria thereby reducing the amount of sulphuric acid input in the treatment of dry yeast.

The use of the three components described above for controlling the microbial contamination in alcoholic fermentation processes can be made through the present antimicrobial composition, or in the form of powder, gel, paste, liquid, pill or tablet, or also with the components separately, for addition to the fermentation must.

The following table shows the performance of the composition in the present alcoholic fermentation process in relation to the results regarding reduction of the fermentative yeasts, wild yeasts, *Lactobacilli* and bacteria present in the fermentative must.

TABLE 1

| N° | Samples | WLN UFC/mL *Saccharomyces cerevisiae* | WLN+ UFC/mL Wild yeast | MRS UFC/mL Lactobacilli | TSA UFC/mL bacteria |
|---|---|---|---|---|---|
| 01 | Kamoran 3 ppm | $1 \times 10^5$ | $2 \times 10^4$ | $2.5 \times 10^2$ | $7 \times 10^3$ |
| 02 | 15 ppm PHMB + 1 ppm Kamoran | $3 \times 10^5$ | $2 \times 10^6$ | <10 | $4 \times 10^1$ |
| 03 | 15 ppm PHMB + 1 ppm Kamoran + 0.05% genapol | $1.2 \times 10^6$ | $3 \times 10^5$ | <10 | $1.4 \times 10^2$ |
| 04 | Blank | $1.3 \times 10^6$ | $9.5 \times 10^6$ | $3.1 \times 10^6$ | $6 \times 10^5$ |

Table 1 above shows the reduction of fermentative yeast, wild yeast, *Lactobacilli* and other bacteria in the fermentative must when it is treated with: an antibiotic agent (Kamoran) only; a composition comprising the antibiotic agent (Kamoran) and an antimicrobial agent (PHMB); and a composition comprising the antibiotics (Kamoran), the antimicrobial agent (PHMB) and the surfactant agent (Genapol).

As can be observed, the use of an antibiotic agent (Kamoran) only, in an amount of 3 ppm of the load of must in fermentation (sample 1), has lead, in relation to the control sample 4, to a reduction of about 1 log in the yeast; of about 3 log in the wild yeast; of about 4 log in the *Lactobacilli* and of about 2 log in other bacteria. As can be seen, the antibiotic action is effective for providing a substantial and positive reduction of the microbiota of contaminants, but also provides an undesirable reduction in the fermentative yeast, not allowing an increase in the efficiency of fermentative processes.

In sample 2, it was used a composition comprising 15 ppm of PHMB (antimicrobial agent) and 1 ppm of Kamoran (antibiotic agent). This composition has provided, in relation to the control sample 4, a reduction of about 1 log in the amount fermentative yeast; of about 1 log in the amount wild yeast; of about 6 log in the amount of *Lactobacilli*; and of about 4 log in amount of other bacteria. As can be seen, the action of the antimicrobial agent together with antibiotic agent has proved to be effective for providing a positive reduction of the microbiota of contaminants, even considering that the reduction in the amount of the wild yeast was inferior to that one obtained with the antibiotic agent only (sample 1). However, this composition also provides an undesirable reduction in the fermentative yeast, not allowing an increase in the efficiency of the fermentative process.

In sample 3, it was used a composition comprising an antimicrobial agent (15 ppm of PHMB); an antibiotic agent (1 ppm of Kamoran); and a surfactant agent (0,05% de Genapol). This composition, which is that one object of the present invention, has provided a reduction of about 2 log in the amount of wild yeast; a reduction of about 6 log in the amount of *Lactobacilli*; and a reduction of about 3 log in the amount of other bacteria.

The combined use of PHMB, antibiotic agent and surfactant agent, in the indicated proportions, has produced an effective reduction of the microbiota of contaminants, without affecting the fermentative yeasts (*Saccharomices cerevisiae*), allowing to obtain an increase in the efficiency of the fermentative process considered herein.

The invention was described with reference to possible embodiments of the invention, as well as the preferred forms of applications. However, it should be understood that many variations and modifications can be made, provided that they fall within the spirit and scope of protection of the enclosed claims.

What is claimed is:

1. An antimicrobial composition for controlling the microbial contamination in alcoholic fermentation processes, comprising an antimicrobial agent of the guanidine family; monensin; and a surfactant, in adequate amounts sufficient to control contaminants being wild yeast, Lactobacilli and bacteria microbiota contained in fermentation medium; to produce a defloculation effect in said fermentation medium; and to preserve the fermentative yeasts from the competition, with contaminants, for sugar contained in the fermentation medium, wherein the antimicrobial composition comprises from 1% to 5%, by weight, of the antimicrobial agent of the guanidine family; from 0.05% to 0.5%, by weight, of monensin; and from 94.5% to 98.95%, by weight, of the surfactant, wherein said surfactant is non-ionic and includes alkoxylated alcohols of the general formula: $R—(OCH_2CH_2)_N—OH$, wherein R is linear or branched, $C_8$-$C_{18}$ alkyl or hydroxyalkyl and N is 1-14.

2. The antimicrobial composition as set forth in claim 1, wherein the antimicrobial agent of the guanidine family is polyhexamethylene biguanide (PHMB).

3. The antimicrobial composition as set forth in claim 1, further comprising a surfactant selected from the group consisting of coconut fatty alcohol, polyglycol ether, cationic surfactants, amphoteric surfactants and other types of nonionic surfactants.

4. The antimicrobial composition as set forth in claim 1, in the form of powder, pill, tablet or liquid for addition to the fermentation medium.

5. A process for controlling the microbial contamination in alcoholic fermentation processes; the process comprising a step of adding to the fermentation medium the antimicrobial composition as set forth in claim 1 to produce a defloculation effect in said fermentation medium; and to preserve the fermentative yeast from the competition, with the contaminants, for the sugar contained in the fermentation medium.

6. The process, as set forth in claim 5, wherein the fermentation medium comprises about 5 ppm to about 26 ppm of the antimicrobial agent of the guanidine family; about 0.26 ppm to about 2.6 ppm of the monensin; and about 491 ppm to about 514 ppm of the surfactant, by weight, of the load of the fermentation medium.

7. The process, as set forth in claim 5, wherein the antimicrobial agent of the guanidine family is polyhexamethylene biguanide (PHMB).

8. The process, as set forth in claim 5, wherein the surfactant further comprises an agent selected from the group consisting of coconut fatty alcohol, polyglycol ethers, cationic surfactants, amphoteric surfactants and other types of non-ionic surfactants.

9. The process, as set forth in claim 5, wherein the biocidal, monensin and surfactant agents are in the form of powder, pill, tablet or liquid for addition to the fermentation medium.

* * * * *